US012740969B2

(12) United States Patent
Muthusamy et al.

(10) Patent No.: US 12,740,969 B2
(45) Date of Patent: Sep. 22, 2026

(54) SOLID STATE FORMS OF TIDEGLUSIB AND PROCESS FOR PREPARATION THEREOF

(71) Applicant: ASSIA CHEMICAL INDUSTRIES LTD., Tel Aviv (IL)

(72) Inventors: Anantha Rajmohan Muthusamy, Sivakasi (IN); Meenakshi Sundaram Somasundaram, Virudu Nagar Dt (IN)

(73) Assignee: ASSIA CHEMICAL INDUSTRIES LTD., Tel Aviv (IL)

( * ) Notice: Subject to any disclaimer, the term of this patent is extended or adjusted under 35 U.S.C. 154(b) by 597 days.

(21) Appl. No.: 18/274,765

(22) PCT Filed: Feb. 23, 2022

(86) PCT No.: PCT/US2022/017424
§ 371 (c)(1),
(2) Date: Jul. 28, 2023

(87) PCT Pub. No.: WO2022/182699
PCT Pub. Date: Sep. 1, 2022

(65) Prior Publication Data

US 2024/0173304 A1 May 30, 2024

(30) Foreign Application Priority Data

Feb. 24, 2021 (IN) ............................ 202111007819

(51) Int. Cl.
*A61K 31/433* (2006.01)

(52) U.S. Cl.
CPC ................................ *A61K 31/433* (2013.01)

(58) Field of Classification Search
CPC .................................................. A61K 31/433
See application file for complete search history.

(56) References Cited

U.S. PATENT DOCUMENTS 8,158,661 B2 * 4/2012 Medina Padilla ...... A61P 35/02 514/361

FOREIGN PATENT DOCUMENTS

WO 2005097117 A1 10/2005

OTHER PUBLICATIONS

Mino R. Caira, "Crystalline Polymorphism Of Organic Compounds", Topics in Current Chemistry, Jan. 1, 1998, vol. 198, pp. 163-208.
International Search Report and Written Opinion of the International Searching Authority issued in corresponding application PCT/US2022/017424 mailed May 24, 2022 (14 pages).

* cited by examiner

*Primary Examiner* — Kamal A Saeed
(74) *Attorney, Agent, or Firm* — Carter, DeLuca & Farrell LLP

(57) ABSTRACT

The present disclosure encompasses solid state forms of Tideglusib, in embodiments crystalline polymorphs or salts or co-crystals of Tideglusib, processes for preparation thereof, and pharmaceutical compositions thereof.

11 Claims, 1 Drawing Sheet

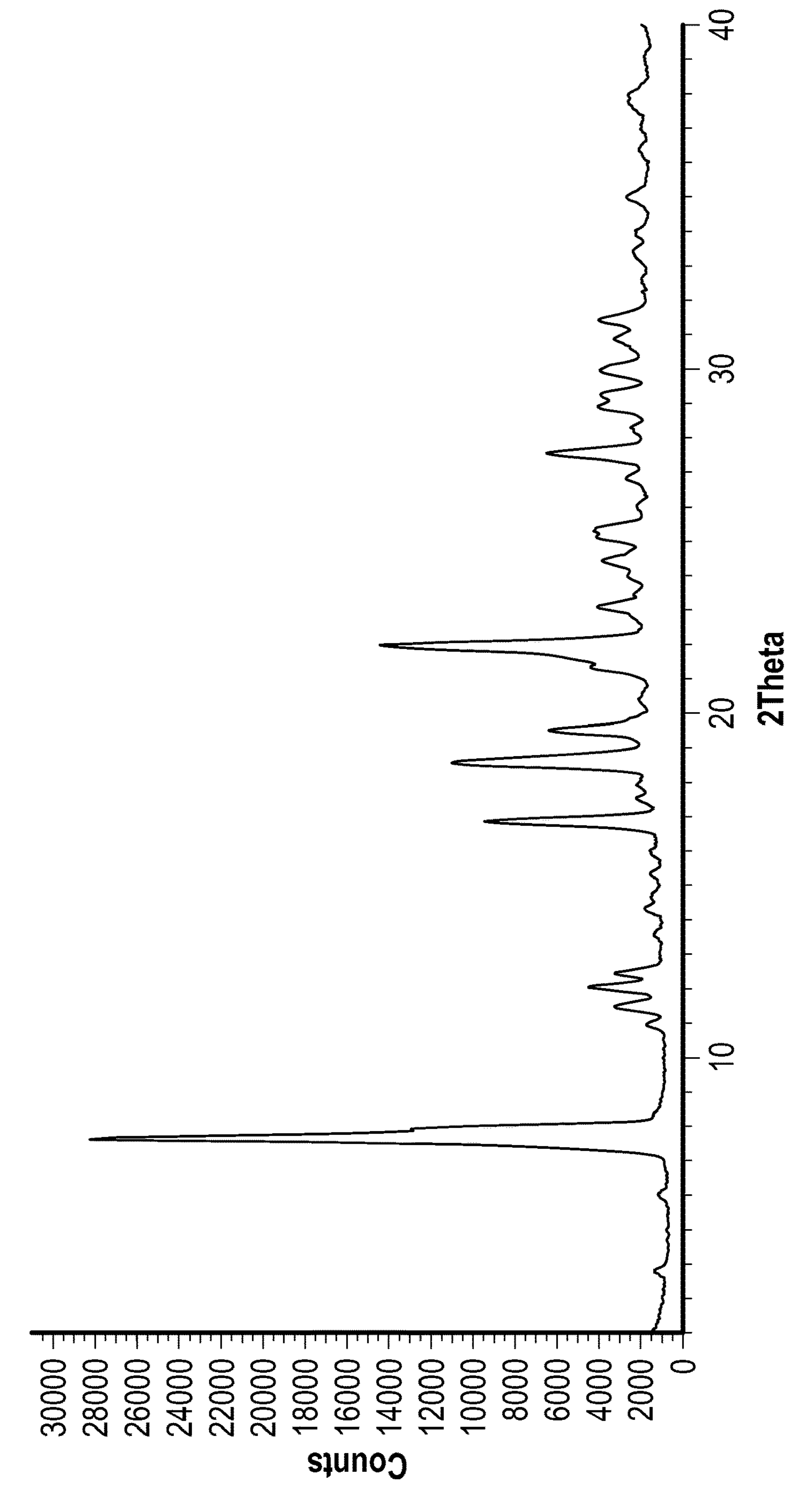
X-Ray Powder Diffraction Pattern of crystalline Tideglusib: L-Proline Form TGC1
Counts
30000
28000
26000
24000
22000
20000
18000
16000
14000
12000
10000
8000
6000
4000
2000
0
10
20
30
40
2Theta

SOLID STATE FORMS OF TIDEGLUSIB AND PROCESS FOR PREPARATION THEREOF

CROSS REFERENCE TO RELATED APPLICATIONS

This application is a National Stage of, and claims priority to and the benefit of, International Patent Application No. PCT/US2022/017424, filed on Feb. 23, 2022, which, in turn, claims the benefit of and priority to, Indian Provisional Application No. 20/211,1007819, filed on Feb. 24, 2021, the entire disclosures of each of which are incorporated by reference herein.

FIELD OF THE DISCLOSURE

The present disclosure encompasses solid state forms of Tideglusib, in embodiments, crystalline polymorphs or salts or co-crystals of Tideglusib, processes for preparation thereof, and pharmaceutical compositions thereof.

BACKGROUND OF THE DISCLOSURE

Tideglusib, 4-Benzyl-2-(naphthalen-1-yl)-1,2,4-thiadiazolidine-3,5-dione, has the following chemical structure:

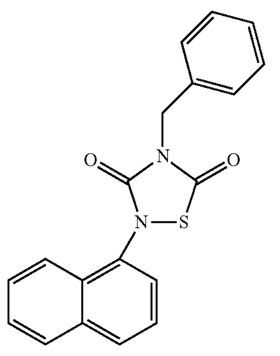 [SMILES: O=c1sn(-c2cccc3ccccc23)c(=O)n1Cc1ccccc1]

Tideglusib is an inhibitor of glycogen synthase kinase 3 beta (GSK-3β) and it is developed for the treatment of myotonic dystrophy. Tideglusib has also been investigated for the treatment of: amyotrophic lateral sclerosis (ALS), autism spectrum disorder, and progressive supranuclear palsy. Tideglusib is also being investigated as a treatment for dental cavities.

The compound is described in International Publication No. WO2005/097117.

Polymorphism, the occurrence of different crystalline forms, is a property of some molecules and molecular complexes. A single molecule may give rise to a variety of polymorphs having distinct crystal structures and physical properties like melting point, thermal behaviors (e.g., measured by thermogravimetric analysis ("TGA"), or differential scanning calorimetry ("DSC")), X-ray diffraction (XRD) pattern, infrared absorption fingerprint, and solid state ($^{13}C$) NMR spectrum. One or more of these techniques may be used to distinguish different polymorphic forms of a compound.

Different salts and solid state forms (including solvated forms) of an active pharmaceutical ingredient may possess different properties. Such variations in the properties of different salts and solid state forms and solvates may provide a basis for improving formulation, for example, by facilitating better processing or handling characteristics, changing the dissolution profile in a favorable direction, or improving stability (polymorph as well as chemical stability) and shelf-life. These variations in the properties of different salts and solid state forms may also offer improvements to the final dosage form, for instance, if they serve to improve bioavailability. Different salts and solid state forms and solvates of an active pharmaceutical ingredient may also give rise to a variety of polymorphs or crystalline forms, which may in turn provide additional opportunities to assess variations in the properties and characteristics of a solid active pharmaceutical ingredient.

Discovering new solid state forms and solvates of a pharmaceutical product may yield materials having desirable processing properties, such as ease of handling, ease of processing, storage stability, and ease of purification or as desirable intermediate crystal forms that facilitate conversion to other polymorphic forms. New solid state forms of a pharmaceutically useful compound can also provide an opportunity to improve the performance characteristics of a pharmaceutical product. It enlarges the repertoire of materials that a formulation scientist has available for formulation optimization, for example by providing a product with different properties, including a different crystal habit, higher crystallinity, or polymorphic stability, which may offer better processing or handling characteristics, improved dissolution profile, or improved shelf-life (chemical/physical stability). For at least these reasons, there is a need for additional solid state forms (including solvated forms and co-crystals) of Tideglusib.

SUMMARY OF THE DISCLOSURE

The present disclosure provides crystalline polymorphs or salts or co-crystals of Tideglusib, processes for preparation thereof, and pharmaceutical compositions thereof. These crystalline polymorphs can be used to prepare other solid state forms of Tideglusib, Tideglusib salts and their solid state forms.

In embodiments, the present disclosure provides crystalline polymorphs or salts or co-crystals of Tideglusib. In embodiments, the present disclosure provides Tideglusib:L-Proline. In embodiments, the present disclosure provides a co-crystal of Tideglusib:L-Proline. In embodiments, the present disclosure provides co-crystal of Tideglusib designated as Form TGC1.

The present disclosure further provides processes for the preparation of the Tideglusib:L-Proline as described in any aspect or embodiment disclosed herein.

The present disclosure also provides uses of the said solid state forms of Tideglusib or salts or co-crystals thereof in the preparation of other solid state forms of Tideglusib or salts or co-crystals thereof.

The present disclosure provides crystalline polymorphs of Tideglusib, including Tideglusib salts or co-crystals of Tideglusib for use in medicine, optionally for treating myotonic dystrophy, amyotrophic lateral sclerosis (ALS), autism spectrum disorder, progressive supranuclear palsy or for treating dental cavities, and more preferably for treating myotonic dystrophy.

The present disclosure also encompasses the use of crystalline polymorphs of Tideglusib, including Tideglusib salts or co-crystals of Tideglusib, of the present disclosure for the preparation of pharmaceutical compositions and/or formulations.

In another aspect, the present disclosure provides pharmaceutical compositions comprising crystalline polymorphs of Tideglusib, including Tideglusib salts or co-crystals of Tideglusib according to the present disclosure.

The present disclosure includes processes for preparing the above mentioned pharmaceutical compositions. The processes include combining any one or a combination of the crystalline polymorphs of Tideglusib, including Tideglusib salts or co-crystals of Tideglusib, with at least one pharmaceutically acceptable excipient.

The crystalline polymorph of Tideglusib, including Tideglusib salts or co-crystals of Tideglusib as defined herein and the pharmaceutical compositions or formulations of the crystalline polymorph of Tideglusib may be used as medicaments, particularly for treating myotonic dystrophy, amyotrophic lateral sclerosis (ALS), autism spectrum disorder, progressive supranuclear palsy or for treating dental cavities, and more preferably for treating myotonic dystrophy.

The present disclosure also provides methods of treating myotonic dystrophy, amyotrophic lateral sclerosis (ALS), autism spectrum disorder, progressive supranuclear palsy or for treating dental cavities, and more preferably for treating myotonic dystrophy, by administering a therapeutically effective amount of any one or a combination of the crystalline polymorphs of Tideglusib, including Tideglusib salts or co-crystals of Tideglusib of the present disclosure, or at least one of the above pharmaceutical compositions, to a subject suffering from myotonic dystrophy, amyotrophic lateral sclerosis (ALS), autism spectrum disorder, progressive supranuclear palsy or dental cavities, and more preferably myotonic dystrophy, or otherwise in need of the treatment.

The present disclosure also provides uses of crystalline polymorphs of Tideglusib, including Tideglusib salts or co-crystals of Tideglusib of the present disclosure, or at least one of the above pharmaceutical compositions, for the manufacture of medicaments for treating myotonic dystrophy, amyotrophic lateral sclerosis (ALS), autism spectrum disorder, progressive supranuclear palsy or treating dental cavities, and more preferably for treating myotonic dystrophy.

BRIEF DESCRIPTION OF THE DRAWINGS

FIG. 1 shows a characteristic X-ray powder diffraction pattern (XRPD) of crystalline Tideglusib:L-Proline Form TGC1.

DETAILED DESCRIPTION OF THE DISCLOSURE

The present disclosure encompasses solid state forms of Tideglusib, including crystalline polymorphs of Tideglusib or Tideglusib salts or co-crystals of Tideglusib, processes for preparation thereof, and pharmaceutical compositions thereof.

In embodiments, the present disclosure provides crystalline polymorphs or salts or co-crystals of Tideglusib. In embodiments, the present disclosure provides a co-crystal of Tideglusib:L-Proline. In embodiments, the present disclosure provides a co-crystal of Tideglusib designated as Form TGC1.

Solid state properties of Tideglusib and crystalline polymorphs thereof can be influenced by controlling the conditions under which Tideglusib and crystalline polymorphs thereof are obtained in solid form.

A solid state form (or polymorph) may be referred to herein as polymorphically pure or as substantially free of any other solid state (or polymorphic) forms. As used herein in this context, the expression "substantially free of any other forms" will be understood to mean that the solid state form contains about 20% (w/w) or less, about 10% (w/w) or less, about 5% (w/w) or less, about 2% (w/w) or less, about 1% (w/w) or less, or about 0% of any other forms of the subject compound as measured, for example, by XRPD. Thus, a crystalline polymorph of Tideglusib described herein as substantially free of any other solid state forms would be understood to contain greater than about 80% (w/w), greater than about 90% (w/w), greater than about 95% (w/w), greater than about 98% (w/w), greater than about 99% (w/w), or about 100% of the subject crystalline polymorph of Tideglusib. In some embodiments of the disclosure, the described crystalline polymorph of Tideglusib may contain from about 1% to about 20% (w/w), from about 5% to about 20% (w/w), or from about 5% to about 10% (w/w) of one or more other crystalline polymorph of the same Tideglusib.

Depending on which other crystalline polymorphs a comparison is made, the crystalline polymorphs of Tideglusib of the present disclosure may have advantageous properties selected from at least one of the following: chemical purity, flowability, solubility, dissolution rate, morphology or crystal habit, stability, such as chemical stability as well as thermal and mechanical stability with respect to polymorphic conversion, stability towards dehydration and/or storage stability, low content of residual solvent, a lower degree of hygroscopicity, flowability, and advantageous processing and handling characteristics such as compressibility and bulk density.

A solid state form, such as a crystal form or an amorphous form, may be referred to herein as being characterized by graphical data "as depicted in" or "as substantially depicted in" a FIGURE. Such data include, for example, powder X-ray diffractograms and solid state NMR spectra. As is well-known in the art, the graphical data potentially provides additional technical information to further define the respective solid state form (a so-called "fingerprint") which cannot necessarily be described by reference to numerical values or peak positions alone. In any event, the skilled person will understand that such graphical representations of data may be subject to small variations, e.g., in peak relative intensities and peak positions due to certain factors such as, but not limited to, variations in instrument response and variations in sample concentration and purity, which are well known to the skilled person. Nonetheless, the skilled person would readily be capable of comparing the graphical data in the FIGURES herein with graphical data generated for an unknown crystal form and confirm whether the two sets of graphical data are characterizing the same crystal form or two different crystal forms. A crystal form of Tideglusib referred to herein as being characterized by graphical data "as depicted in" or "as substantially depicted in" a FIGURE will thus be understood to include any crystal forms of Tideglusib characterized with the graphical data having such small variations, as are well known to the skilled person, in comparison with the FIGURE.

As used herein, and unless stated otherwise, the term "anhydrous" in relation to crystalline forms of Tideglusib, relates to a crystalline form of Tideglusib which does not include any crystalline water (or other solvents) in a defined, stoichiometric amount within the crystal. Moreover, an "anhydrous" form would generally not contain more than 1% (w/w), of either water or organic solvents as measured for example by TGA.

The term "solvate," as used herein and unless indicated otherwise, refers to a crystal form that incorporates a solvent in the crystal structure. When the solvent is water, the solvate is often referred to as a "hydrate." The solvent in a solvate may be present in either a stoichiometric or in a non-stoichiometric amount.

As used herein, the term "isolated" in reference to crystalline polymorph of Tideglusib of the present disclosure corresponds to a crystalline polymorph of Tideglusib that is physically separated from the reaction mixture in which it is formed.

As used herein, unless stated otherwise, the XRPD measurements are taken using copper Kα radiation wavelength 1.5418 Å. XRPD peaks reported herein are measured using CuKα radiation, $\lambda$=1.5418 Å, typically at a temperature of 25±3° C.

As used herein, unless stated otherwise, $^{13}C$ NMR reported herein are measured at 125 MHz at a magic angle spinning frequency $\omega_r/2\pi$=11 kHz, preferably at a temperature of at 293 K±3° C.

A thing, e.g., a reaction mixture, may be characterized herein as being at, or allowed to come to "room temperature" or "ambient temperature", often abbreviated as "RT." This means that the temperature of the thing is close to, or the same as, that of the space, e.g., the room or fume hood, in which the thing is located. Typically, room temperature is from about 20° C. to about 30° C., or about 22° C. to about 27° C., or about 25° C.

The amount of solvent employed in a chemical process, e.g., a reaction or crystallization, may be referred to herein as a number of "volumes" or "vol" or "V." For example, a material may be referred to as being suspended in 10 volumes (or 10 vol or 10V) of a solvent. In this context, this expression would be understood to mean milliliters of the solvent per gram of the material being suspended, such that suspending a 5 grams of a material in 10 volumes of a solvent means that the solvent is used in an amount of 10 milliliters of the solvent per gram of the material that is being suspended or, in this example, 50 mL of the solvent. In another context, the term "v/v" may be used to indicate the number of volumes of a solvent that are added to a liquid mixture based on the volume of that mixture. For example, adding solvent X (1.5 v/v) to a 100 ml reaction mixture would indicate that 150 mL of solvent X was added.

A process or step may be referred to herein as being carried out "overnight." This refers to a time interval, e.g., for the process or step, that spans the time during the night, when that process or step may not be actively observed. This time interval is from about 8 to about 20 hours, or about 10-18 hours, in some cases about 16 hours.

As used herein, the term "reduced pressure" refers to a pressure that is less than atmospheric pressure. For example, reduced pressure is about 10 mbar to about 50 mbar.

As used herein and unless indicated otherwise, the term "ambient conditions" refer to atmospheric pressure and a temperature of 22-24° C.

"Co-Crystal" or "Co-crystal" as used herein is defined as a crystalline material including two or more molecules in the same crystalline lattice and associated by non-ionic and non-covalent bonds. In some embodiments, the co-crystal includes two molecules which are in natural state. In an embodiments the molar ratio between the active pharmaceutical ingredient (Tideglusib) and the coformer (L-Proline) is between 1:1.5 and 1.5:1, preferably between 1:1.25 and 1.25:1, in other embodiments about 1:1.

As used herein, crystalline Tideglusib:L-Proline is a distinct molecular species. Crystalline Tideglusib:L-Proline may be a co-crystal of Tideglusib and L-Proline. Alternatively crystalline Tideglusib:L-Proline may be a salt.

The present disclosure further encompasses crystalline Tideglusib:L-Proline. The present disclosure also encompasses a co-crystal of Tideglusib with a co-crystal former, particularly a co-crystal of Tideglusib:L-Proline. The crystalline Tideglusib:L-Proline may be a co-crystal of Tideglusib and L-Proline. Alternatively, crystalline Tideglusib:L-Proline may be a salt.

Preferably, crystalline Tideglusib:L-Proline according to the invention is co-crystal of Tideglusib and L-Proline.

The disclosure further encompasses a crystalline form of Tideglusib and L-Proline, designated form TGC1. Crystalline Form TGC1 of Tideglusib:L-Proline may be characterized by data selected from one or more of the following: an X-ray powder diffraction pattern substantially as depicted in FIG. 1; an X-ray powder diffraction pattern having peaks at 11.5, 12.5, 18.6, 22.0 and 23.1 degrees 2-theta±0.2 degrees 2-theta; and combinations of these data.

Crystalline Form TGC1 of Tideglusib:L-Proline may be further characterized by an X-ray powder diffraction pattern having peaks at 11.5, 12.5, 18.6, 22.0 and 23.1 degrees 2-theta±0.2 degrees 2-theta, and also having any one, two, three, four or five additional peaks selected from 7.7, 16.8, 19.5, 27.6 and 29.1 degrees 2-theta±0.2 degrees 2-theta.

Crystalline Form TGC1 of Tideglusib:L-Proline may be alternatively characterized by an X-ray powder diffraction pattern having peaks at 7.7, 11.5, 12.5, 16.8, 18.6, 19.5, 22.0, 23.1, 27.6 and 29.1 degrees 2-theta±0.2 degrees 2-theta.

According to any aspect or embodiment of the disclosure, the molar ratio between Tideglusib and L-Proline may be 1:1.

In any aspect or embodiments of the present disclosure, the co-crystal of Tideglusib with L-Proline, particularly the crystalline Form TGC1 of Tideglusib:L-Proline, is isolated.

According to any aspect or embodiment of the disclosure, the co-crystal of Tideglusib with L-proline, particularly the crystalline Form TGC1 of Tideglusib:L-Proline, may be an anhydrous form.

Crystalline Form TGC1 of Tideglusib:L-Proline may be characterized by each of the above characteristics alone or by all possible combinations, e.g., an XRPD pattern having peaks at 11.5, 12.5, 18.6, 22.0 and 23.1 degrees 2-theta±0.2 degrees 2-theta; an XRPD pattern as depicted in FIG. 1; and combinations thereof.

In any aspect or embodiment of the present disclosure, the crystalline of Tideglusib:L-Proline, particularly the crystalline Form TGC1 of Tideglusib:L-Proline, may be polymorphically pure or may be substantially free of any other solid state forms of Tideglusib or Tideglusib:L-Proline. In particular, the crystalline Tideglusib:L-Proline, particularly the crystalline Form TGC1 of Tideglusib:L-Proline described in any aspect or embodiment disclosed herein, may contain: about 20% (w/w) or less, about 10% (w/w) or less, about 5% (w/w) or less, about 2% (w/w) or less, about 1% (w/w) or less, about 0.5% (w/w) or less, about 0.2% (w/w) or less, about 0.1% (w/w) or less, or about 0%, of any other solid state forms of Tideglusib or Tideglusib:L-Proline, preferably as measured by XRPD. Thus, the crystalline form of Tideglusib:L-Proline, particularly the crystalline Form TGC1 of Tideglusib:L-Proline, may be substantially free of any other solid state forms of Tideglusib or Tideglusib:L-Proline, and may contain greater than about 80% (w/w), greater than about 90% (w/w), greater than about 95% (w/w), greater than about 98% (w/w), greater than about 99% (w/w), or about 100% of the subject solid state form of Tideglusib:L-Proline, particularly the crystalline Form TGC1 of Tideglusib:L-Proline.

The above crystalline polymorphs can be used to prepare other crystalline polymorphs of Tideglusib, Tideglusib salts and their solid state forms.

The present disclosure further provides a process for preparing crystalline Tideglusib:L-proline, preferably crystalline Form TGC1 of Tideglusib:L-Proline, as described in any aspect or embodiment of the disclosure.

The process comprises crystallising Tideglusib:L-proline from at least one polar solvent. Preferably, the polar solvent may comprise a $C_3$-$C_6$ ketone (particularly a $C_3$-$C_4$ ketone, and more preferably acetone) or a $C_1$-$C_6$ alcohol (preferably a $C_1$-$C_4$ alcohol, a $C_1$-$C_3$ alcohol, and more preferably methanol), or a mixture of a ketone and an alcohol.

According to any aspect or embodiment of the disclosed processes, the process may comprise:

(i) providing a solution of Tideglusib in at least one polar solvent;
(ii) combining the solution with L-Proline;
(iii) cooling the mixture; optionally
(iv) isolating Tideglusib; L-Proline from the mixture; and optionally
(v) drying the Tideglusib:L-Proline.

According to any aspect or embodiment of the disclosed process, the process may comprise the following steps:

(i) dissolving Tideglusib in acetone, preferably a $C_3$-$C_6$ ketone;
(ii) adding L-Proline solution, preferably wherein the L-Proline is in a solution with an alcohol, particularly a $C_1$-$C_6$ alcohol);
(iii) cooling; optionally
(iv) isolating Tideglusib L-Proline; and optionally
(v) drying the Tideglusib L-Proline.

According to any aspect or embodiment of the disclosed processes, L-Proline may be added in an amount of about 1 to about 1.5, about 1 to about 1.2, about 1 to about 1.1, about 1 to about 1.05, or about 1 molar equivalents relative to Tideglusib.

According to any aspect or embodiment of the disclosed processes, L-Proline may be added as a solid, or preferably as a solution. Particularly, the L-Proline may be added as a solution in a polar solvent, particularly a $C_1$-$C_6$, or a $C_1$-$C_3$ alcohol. The solution may comprise L-Proline and solvent in an amount of about 2 to about 30 ml, about 5 to about 20 ml, about 5 about 15 ml, or about 10 ml of solvent per gram of L-Proline.

In any aspect or embodiment of the disclosed processes, step (i) may be conducted at a temperature of about 45° C. to about 70° C., or about 50° C. to about 65° C., or about 60° C.

In any aspect or embodiment of the disclosed processes, the solvent in step (i) may be used in an amount of about 10 ml to about 30 ml, about 15 ml to about 25 ml, about 17 ml to about 22 ml, or about 20 ml, per gram of Tideglusib.

In any aspect or embodiment of the disclosed processes, step (ii) may be carried out at a temperature of about 45° C. to about 70° C., or about 50° C. to about 65° C.

In any aspect or embodiment of the disclosed processes, the mixture in step (ii) may be held at elevated temperature, particularly at a temperature of about 45° C. to about 70° C., or about 50° C. to about 65° C., or about 60° C. According to any aspect or embodiment of the disclosed processes, the mixture may be held for a period of about 5 to about 100 minutes, about 10 to about 80 minutes, about 20 to about 50 minutes, about 25 to about 40 minutes, or about 30 minutes.

In any embodiment of the process, when the solvent is a mixture of a ketone and an alcohol (particularly acetone and methanol) the ratio (v/v) of ketone to alcohol is about 1:1 to about 1:2.5, about 1:1.2 to about 1:2.2, about 1:1.5 to about 1:2.0, about 1:1.7 to about 1:1.9, or about 1:about 1:1.75 to about 1:1.85, or about 1:1.8.

In any aspect or embodiment of the disclosed processes, the L-Proline is added as a solution in in methanol. The L-Proline is added in methanol in amount of about 10% w/v.

In any aspect or embodiment of the process, step (iii) comprises cooling the mixture typically to a temperature of about 15° C. to about 35° C., about 20° C. to about 30° C., or about 25° C.

In any aspect or embodiment of the process, the mixture may be cooled over a period of about 0.3 hours to about 2 hours, about 0.5 hour to 1.5 hours, or about 1 hour.

In any embodiment of the process, the cooled mixture may be maintained, typically at a temperature of about 15° C. to about 35° C., about 20° C. to about 30° C., or about 25° C., for about 10 hours to about 30 hours, about 12 hours to about 28 hours or about 20 hours.

The process may further include isolating the obtained Tideglusib:L-Proline, by any suitable procedure, such as filtration, decantation, or by centrifuge. Particularly, the product may be isolated by vacuum filtration. Following isolation, the crystalline Tideglusib:L-Proline may be dried. The drying may be carried out during, e.g. filtration for the period of about 15 minutes to 1 hour, or about 10 minutes to about 15 minutes. Optionally or additionally, the Tideglusib:L-Proline may be dried under reduced pressure, typically at a temperature of about 40° C. to about 80° C., about 30° C. to about 55° C., about 40° C. to about 50° C., or about 60° C. The drying may be carried out for any suitable time to remove the solvent (e.g. to a constant weight), typically about 15 minutes to about 1.5 hours, about 20 hours to about 1 hour, or about 30 minutes.

According to any aspect or embodiment of the processes disclosed herein, the processes may further comprise combining the Tideglusib:L-Proline with at least one pharmaceutically acceptable excipient to obtain a pharmaceutical composition or a pharmaceuticals formulation.

The present disclosure encompasses a process for preparing other solid state forms of Tideglusib, Tideglusib salts and their solid state forms thereof. The process includes preparing any one of the Tideglusib (salts) and solid state forms of Tideglusib by the processes of the present disclosure, particularly Tideglusib:L-Proline according to any aspect or embodiment of the present disclosure, and more particularly Tideglusib:L-Proline Form TGC1, and converting that salt or solid state form to said other Tideglusib salt, or other solid state form.

According to any aspect or embodiment of the processes for preparing Tideglusib:L-Proline disclosed herein, the processes may further comprise converting the Tideglusib:L-Proline to Tideglusib, a salt of Tideglusib, or other co-crystal of Tideglusib, and combining the Tideglusib, salt of Tideglusib, or other co-crystal of Tideglusib, with at least one excipient to obtain a pharmaceutical composition or pharmaceutical formulation.

The present disclosure provides the above described crystalline polymorphs of Tideglusib for use in the preparation of pharmaceutical compositions comprising Tideglusib and/or crystalline polymorphs thereof.

The present disclosure also encompasses the use of crystalline polymorphs of Tideglusib of the present disclosure for the preparation of pharmaceutical compositions of crystalline polymorph Tideglusib and/or crystalline polymorphs thereof.

The present disclosure includes processes for preparing the above mentioned pharmaceutical compositions. The processes include combining any one or a combination of the crystalline polymorphs of Tideglusib of the present disclosure with at least one pharmaceutically acceptable excipient.

Pharmaceutical combinations or formulations of the present disclosure contain any one or a combination of the solid state forms of Tideglusib of the present disclosure. In addition to the active ingredient, the pharmaceutical formulations of the present disclosure can contain one or more excipients. Excipients are added to the formulation for a variety of purposes.

Diluents increase the bulk of a solid pharmaceutical composition, and can make a pharmaceutical dosage form containing the composition easier for the patient and caregiver to handle. Diluents for solid compositions include, for example, microcrystalline cellulose (e.g. Avicel®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol, and talc.

Solid pharmaceutical compositions that are compacted into a dosage form, such as a tablet, can include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate, and starch.

The dissolution rate of a compacted solid pharmaceutical composition in the patient's stomach can be increased by the addition of a disintegrant to the composition. Disintegrants include alginic acid, carboxymethylcellulose calcium, carboxymethylcellulose sodium (e.g. Ac-Di-Sol®, Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®), and starch.

Glidants can be added to improve the flowability of a non-compacted solid composition and to improve the accuracy of dosing. Excipients that can function as glidants include colloidal silicon dioxide, magnesium trisilicate, powdered cellulose, starch, talc, and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc, and zinc stearate.

Flavoring agents and flavor enhancers make the dosage form more palatable to the patient. Common flavoring agents and flavor enhancers for pharmaceutical products that can be included in the composition of the present disclosure include maltol, vanillin, ethyl vanillin, menthol, citric acid, fumaric acid, ethyl maltol, and tartaric acid.

Solid and liquid compositions can also be dyed using any pharmaceutically acceptable colorant to improve their appearance and/or facilitate patient identification of the product and unit dosage level.

In liquid pharmaceutical compositions of the present invention, Tideglusib and any other solid excipients can be dissolved or suspended in a liquid carrier such as water, vegetable oil, alcohol, polyethylene glycol, propylene glycol, or glycerin.

Liquid pharmaceutical compositions can contain emulsifying agents to disperse uniformly throughout the composition an active ingredient or other excipient that is not soluble in the liquid carrier. Emulsifying agents that can be useful in liquid compositions of the present invention include, for example, gelatin, egg yolk, casein, cholesterol, acacia, tragacanth, chondrus, pectin, methyl cellulose, carbomer, cetostearyl alcohol, and cetyl alcohol.

Liquid pharmaceutical compositions of the present invention can also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth, xanthan gum and combinations thereof.

Sweetening agents such as sorbitol, saccharin, sodium saccharin, sucrose, aspartame, fructose, mannitol, and invert sugar can be added to improve the taste.

Preservatives and chelating agents such as alcohol, sodium benzoate, butylated hydroxyl toluene, butylated hydroxyanisole, and ethylenediamine tetraacetic acid can be added at levels safe for ingestion to improve storage stability.

According to the present disclosure, a liquid composition can also contain a buffer such as gluconic acid, lactic acid, citric acid, or acetic acid, sodium gluconate, sodium lactate, sodium citrate, or sodium acetate. Selection of excipients and the amounts used can be readily determined by the formulation scientist based upon experience and consideration of standard procedures and reference works in the field.

The solid compositions of the present disclosure include powders, granulates, aggregates, and compacted compositions. The dosages include dosages suitable for oral, buccal, rectal, parenteral (including subcutaneous, intramuscular, and intravenous), inhalant, and ophthalmic administration. Although the most suitable administration in any given case will depend on the nature and severity of the condition being treated, in embodiments the route of administration is oral. The dosages can be conveniently presented in unit dosage form and prepared by any of the methods well-known in the pharmaceutical arts.

Dosage forms include solid dosage forms like tablets, powders, capsules, suppositories, sachets, troches, and lozenges, as well as liquid syrups, suspensions, and elixirs.

The dosage form of the present disclosure can be a capsule containing the composition, such as a powdered or granulated solid composition of the disclosure, within either a hard or soft shell. The shell can be made from gelatin and optionally contain a plasticizer such as glycerin and/or sorbitol, an opacifying agent and/or colorant.

The active ingredient and excipients can be formulated into compositions and dosage forms according to methods known in the art.

A composition for tableting or capsule filling can be prepared by wet granulation. In wet granulation, some or all of the active ingredients and excipients in powder form are blended and then further mixed in the presence of a liquid, typically water, that causes the powders to clump into granules. The granulate is screened and/or milled, dried, and then screened and/or milled to the desired particle size. The granulate can then be tableted, or other excipients can be added prior to tableting, such as a glidant and/or a lubricant.

A tableting composition can be prepared conventionally by dry blending. For example, the blended composition of the actives and excipients can be compacted into a slug or a sheet and then comminuted into compacted granules. The compacted granules can subsequently be compressed into a tablet.

As an alternative to dry granulation, a blended composition can be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate, and colloidal silica. The proper use of these and other excipients in direct compression tableting is known to those in the art with experience and skill in particular formulation challenges of direct compression tableting.

A capsule filling of the present disclosure can include any of the aforementioned blends and granulates that were described with reference to tableting, but they are not subjected to a final tableting step.

A pharmaceutical formulation of Tideglusib can be administered. Tideglusib may be formulated for administration to a mammal, in embodiments to a human, by injection. Tideglusib can be formulated, for example, as a viscous liquid solution or suspension, such as a clear solution, for injection. The formulation can contain one or more solvents. A suitable solvent can be selected by considering the solvent's physical and chemical stability at various pH levels, viscosity (which would allow for syringeability), fluidity, boiling point, miscibility, and purity. Suitable solvents include alcohol USP, benzyl alcohol NF, benzyl benzoate USP, and Castor oil USP. Additional substances can be added to the formulation such as buffers, solubilizers, and antioxidants, among others. Ansel et al., Pharmaceutical Dosage Forms and Drug Delivery Systems, 7th ed.

The crystalline polymorphs of Tideglusib and the pharmaceutical compositions and/or formulations of Tideglusib of the present disclosure can be used as medicaments, preferably for the treatment of myotonic dystrophy, amyotrophic lateral sclerosis (ALS), autism spectrum disorder, progressive supranuclear palsy or for the treatment of dental cavities, and more preferably for the treatment of myotonic dystrophy.

The present disclosure also provides methods of treating myotonic dystrophy, amyotrophic lateral sclerosis (ALS), autism spectrum disorder, progressive supranuclear palsy or for treating dental cavities, and more preferably treating myotonic dystrophy, by administering a therapeutically effective amount of any one or a combination of the crystalline polymorphs of Tideglusib of the present disclosure, or at least one of the above pharmaceutical compositions and/or formulations, to a subject in need of the treatment.

Having thus described the disclosure with reference to particular preferred embodiments and illustrative examples, those in the art can appreciate modifications to the disclosure as described and illustrated that do not depart from the spirit and scope of the disclosure as disclosed in the specification. The Examples are set forth to aid in understanding the disclosure but are not intended to, and should not be construed to limit its scope in any way.

Powder X-Ray Diffraction ("XRPD") Method

X-ray diffraction was performed on X-Ray powder diffractometer: Bruker D8 Advance; CuKα radiation (λ=1.5418 Å); Lynx eye detector; laboratory temperature 22-25° C.; PMMA specimen holder ring with silicon low background. Prior to analysis, the samples were gently ground by means of mortar and pestle in order to obtain a fine powder. The ground sample was adjusted into a cavity of the sample holder and the surface of the sample was smoothed by means of a cover glass.

Measurement Parameters:

- Scan range: 2-40 degrees 2-theta;
- Scan mode: continuous;
- Step size: 0.05 degrees;
- Time per step: 0.5 s;
- Sample spin: 30 rpm;
- Sample holder: PMMA specimen holder ring with silicon low background.

All X-Ray Powder Diffraction peak values are calibrated with regard to standard silicon spiking in the sample.

EXAMPLES

Preparation of Starting Materials

Tideglusib can be prepared according to methods known from the literature, for example, following Example 2 disclosed in U.S. Pat. No. 7,531,561.

Example 1: Preparation of Crystalline Tideglusib:L-Proline Form TGC1

Tideglusib (0.05 grams) was taken in a 10 mL test tube and was dissolved in 1 mL Acetone at temperature of about 60° C. L-Proline solution (10% w/v in methanol) (1.8 mL) was added in 1:1 molar ratio (Tideglusib:L-Proline) and maintained at temperature of about 60° C. for period of about 30 minutes. The reaction mixture was cooled to temperature of about 25° C. in a period of about 1 hour and stirred at temperature of about 25° C. for a period of about 20 hours. The reaction mass was filtered and dried under vacuum for period of about 10 minutes to about 15 minutes. The obtained solid was dried at temperature of about 60° C. for period of about 30 minutes. The obtained solid was analyzed by XRPD. Crystalline Tideglusib:L-Proline Form TGC1 was obtained. An XRPD pattern is shown in FIG. 1.

The invention claimed is:

1. Crystalline Tideglusib: L-Proline, which is a co-crystal, which is characterized by data selected from:

a. an X-ray powder diffraction pattern having peaks at 11.5, 12.5, 18.6, 22.0 and 23.1 degrees 2-theta±0.2 degrees 2-theta; or b. an X-ray powder diffraction pattern as depicted in FIG. 1.

2. The crystalline Tideglusib: L-Proline according to claim 1, which is characterized by an X-ray powder diffraction pattern having peaks at 11.5, 12.5, 18.6, 22.0 and 23.1 degrees 2-theta±0.2 degrees 2-theta, and also having any one, two, three, four or five additional peaks selected from 7.7, 16.8, 19.5, 27.6 and 29.1 degrees 2-theta±0.2 degrees 2-theta.

3. The crystalline Tideglusib: L-Proline according to claim 1, wherein said co-crystal is anhydrous.

4. The crystalline Tideglusib: L-Proline according to claim 1, wherein molar ratio of Tideglusib and L-proline is about 1:1.

5. The crystalline Tideglusib: L-Proline according to claim 1, which contains about 20% or less of any other solid state forms of Tideglusib or Tideglusib: L-Proline.

6. A pharmaceutical composition comprising the crystalline Tideglusib: L-Proline according to claim 1.

7. A pharmaceutical formulation comprising the crystalline Tideglusib: L-Proline according to claim 1 with at least one pharmaceutically acceptable excipient.

8. A process comprising combining the crystalline Tideglusib: L-Proline according to claim 1 with at least one pharmaceutically acceptable excipient.

9. A method of treating myotonic dystrophy, amyotrophic lateral sclerosis (ALS), autism spectrum disorder, progressive supranuclear palsy or treating dental cavities, comprising administering a therapeutically effective amount of the crystalline Tideglusib: L-Proline according to claim 1 to a subject in need of the treatment.

10. The crystalline Tideglusib: L-Proline according to claim 1, which is characterized by an XRPD pattern having peaks at: 7.7, 11.5, 12.5, 16.8, 18.6, 19.5, 22.0, 23.1, 27.6 and 29.1 degrees 2-theta±0.2 degrees 2-theta.

11. A method of treating myotonic dystrophy comprising administering a therapeutically effective amount of the crystalline Tideglusib: L-Proline according to claim 1 to a subject in need of the treatment.

* * * * *